United States Patent
Ohya et al.

(10) Patent No.: US 8,377,274 B2
(45) Date of Patent: Feb. 19, 2013

(54) GAS SENSOR AND METHOD FOR MANUFACTURING THE SAME

(75) Inventors: Seiji Ohya, Aichi (JP); Tomohiro Wakazono, Konan (JP); Kenji Kato, Nagoya (JP); Koji Shiotani, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 855 days.

(21) Appl. No.: 12/463,625

(22) Filed: May 11, 2009

(65) Prior Publication Data

US 2009/0280240 A1 Nov. 12, 2009

(30) Foreign Application Priority Data

May 12, 2008 (JP) ................................. 2008-124263
Mar. 24, 2009 (JP) ................................. 2009-071806

(51) Int. Cl.
*G01N 27/407* (2006.01)

(52) U.S. Cl. ......... 204/426; 204/421; 204/424; 204/427

(58) Field of Classification Search .......... 204/424–429; 205/780.5–781, 782–785.5
See application file for complete search history.

(56) References Cited

U.S. PATENT DOCUMENTS

| | | | |
|---|---|---|---|
| 6,338,783 B1 * | 1/2002 | Inoue et al. | 204/425 |
| 2002/0005353 A1 | 1/2002 | Kato et al. | |
| 2002/0162755 A1 | 11/2002 | Kato et al. | |
| 2003/0070924 A1 * | 4/2003 | Sugaya et al. | 204/424 |
| 2006/0231397 A1 | 10/2006 | Nakagaki et al. | |
| 2007/0151849 A1 * | 7/2007 | Ishiguro et al. | 204/424 |

FOREIGN PATENT DOCUMENTS

| | | |
|---|---|---|
| JP | 11-183434 A | 7/1999 |
| JP | 2005-283240 A | 10/2005 |

* cited by examiner

*Primary Examiner* — Keith Hendricks
*Assistant Examiner* — Bach Dinh
(74) *Attorney, Agent, or Firm* — Sughrue Mion, PLLC

(57) ABSTRACT

A gas sensor including a gas sensor element having a first measurement chamber (16); a first pumping cell (11); a second measurement chamber (18) into which a gas to be measured having a controlled oxygen partial pressure is introduced; and a second pumping cell (13) having a second inner pump electrode (13b) and a second counterpart electrode (13c) pump electrode configured to detect a specific gas component. The second inner pump electrode is made of a material that contains, as a principal ingredient, two kinds of Pt particles having different particle sizes and whose particle size ratio measured by a sedimentation particle-size distribution ranges from 1.75 to 14.2. A mixing ratio between large Pt particles and small Pt particles has a mass ratio of 10/90 to 50/50. A 10 kHz-1 Hz resistance value across the second pumping cell at 600° C. is 150Ω or less.

2 Claims, 9 Drawing Sheets

GAS SENSOR AND METHOD FOR MANUFACTURING THE SAME

BACKGROUND OF THE INVENTION

1. Field of the Invention

The present invention relates to a gas sensor having a gas sensor element that detects the concentration of a specific gas, such as NOx, contained in a combustion gas or an exhaust gas of, for instance, a combustor, an engine, and the like, as well as to a method for manufacturing the gas sensor.

2. Description of Related Art

There is a need for further reduction in the amount of nitrogen oxide (NOx) contained in exhaust gas as regulations on the exhaust gas of an engine, such as an automobile, became more strict. In this regard, an NOx sensor capable of directly measuring the concentration of NOx has been developed.

The NOx sensor has a gas sensor element with one or a plurality of cells, each of which has a pair of electrodes formed on the surface of an oxygen-ion-conductive solid electrolyte layer, such as zirconia. A first pumping cell evacuates oxygen in a first measurement chamber while remaining in mutual communication with a second chamber for receiving the gas to be measured. Further, an oxygen concentration detection cell measures the concentration of oxygen in the first measurement chamber and controls the first pumping cell in such a way that a predetermined oxygen concentration is achieved within the first measurement chamber. Moreover, the gas to be measured having a controlled oxygen concentration flows into the second measurement chamber from the first measurement chamber. NOx contained in the gas to be measured is decomposed into $N_2$ and $O_2$ by applying a given voltage to the second pumping cell. A second pump current flowing between a pair of electrodes of the second pumping cell is measured, whereby the concentration of NOx in the gas to be measured is detected.

In such an NOx sensor, an inner second pump electrode of the second pumping cell is provided in the second measurement chamber and has the primary function of pumping the $O_2$ component originating from decomposition of a trace amount of NOx contained in the gas to be measured. In order to enhance durability of the inner second pump electrode, a technique has been developed using, as an electrode material, cermet consisting of a Pt—Rh alloy and ceramic (see Patent Document 1). A technique for using, as a material for the inner second pump electrode, a mixture consisting of Pt—Rh powder and zirconia powder has also been developed (see Patent Document 2).

[Patent Document 1] JP-A-11-183434
[Patent Document 2] JP-A-2005-283240

3. Problems to be Solved by the Invention

The second pumping cell has a primary function of pumping $O_2$ originating from decomposition of a trace amount of NOx gas. The concentration of NOx gas to be pumped is equivalent to several microamperes in terms of a second pump current. Therefore, even in a case where the pumping capability of the second pumping cell is low, the pumping capability is sufficient for decomposing the trace amount of NOx gas at the time of measuring NOx concentration.

In the meantime, at the time of heating the NOx sensor to activate the solid electrolytes of the sensor element so that they are capable of transporting oxygen, it is necessary to forcefully pump out a high concentration of $O_2$ present in the second measurement chamber. In this regard, the pumping capability of the second pumping cell becomes deficient. Consequently, a problem arises in that there is an increase in the length of the so-called light-off time, namely, a duration from the beginning of start-up control of the sensor until the concentration of $O_2$ in the second measurement chamber (the second pump current) is reduced to a given level by pumping.

SUMMARY OF THE INVENTION

Accordingly, an object of the present invention is to provide a gas sensor capable of shortening the light-off time by enhancing the pumping capability of the second pumping cell and a method for manufacturing the gas sensor.

According to a first aspect, the above object of the present invention is achieved by providing a gas sensor including a gas sensor element extending in a longitudinal direction thereof, the gas sensor element comprising: a first measurement chamber interposed between two solid electrolyte layers stacked with an interval therebetween and into which a gas to be measured is introduced from outside the sensor; a first pumping cell having a first inner pump electrode facing the first measurement chamber and a first counterpart electrode for the first inner pump electrode, the first pumping cell being configured to control oxygen partial pressure in the first measurement chamber; a second measurement chamber in mutual communication with the first measurement chamber, that is partitioned from surroundings and into which a gas to be measured having a controlled oxygen partial pressure is introduced from the first measurement chamber; and a second pumping cell having a second inner pump electrode disposed within the second measurement chamber and a second counterpart electrode for the second inner pump electrode, the second pumping cell being configured to detect a specific gas component in the gas to be measured within the second measurement chamber, wherein the second inner pump electrode is made of a material that contains, as a principal ingredient, two kinds of Pt particles having different particle sizes and whose particle size ratio as measured by sedimentation particle-size distribution ranges from 1.75 to 14.2, and which has a mixing ratio of large Pt particles to small Pt particles having a mass ratio of 10/90 to 50/50 (large Pt particles/small Pt particles); and a 10 kHz-1 Hz resistance value across the second pumping cell at 600° C. is 150Ω or less.

With such a configuration, the large Pt particles of the Pt particles included in the second inner pump electrode can prevent the occurrence of a break in the second inner pump electrode, which may otherwise occur due to growth and coagulation of the small Pt particles. Further, the small Pt particles form a coarsely textured electrode over the surface of the solid electrolyte layer, thereby enhancing a triple-layer interface ratio and electrode activity. As a consequence, a 10 kHz-1 Hz resistance value achieved across the second pumping cell becomes 150Ω or less, and the light-off time is shortened as compared with that achieved by a related-art NOx sensor. In addition, the triple-layer interface ratio means a ratio of the triple-layer interface formed in a sensor cell.

In a preferred embodiment of the above first aspect, the second inner pump electrode has an average thickness of 15 μm or less, and the second inner pump electrode has a minimum thickness which ranges from 4 μm to 11 μm.

According to a second aspect, the present invention provides a gas sensor including a gas sensor element extending in a longitudinal direction thereof, the gas sensor element comprising: a first measurement chamber interposed between two solid electrolyte layers stacked with an interval therebetween and into which a gas to be measured is introduced from outside the sensor; a first pumping cell having a first inner pump electrode facing the first measurement chamber and a first counterpart electrode for the first inner pump electrode, the first inner pump electrode being configured to control oxygen partial pressure in the first measurement chamber; a second measurement chamber in mutual communication with the first measurement chamber, that is partitioned from surroundings and into which a gas to be measured having a controlled oxygen partial pressure is introduced from the first measurement chamber; and a second pumping cell having a second inner pump electrode disposed within the second measurement chamber and a second counterpart electrode for the second inner pump electrode, the second pumping cell being configured to detect a specific gas component in the gas to be measured within the second measurement chamber, wherein the second inner pump electrode is made of an aggregate that contains Pt as a principal ingredient consisting of a plurality of Pt particles including larger Pt particles and smaller Pt particles; in a cutting plane of the gas sensor element taken along its stacking direction, when a reflection electron image including an interface between the second inner pump electrode and a solid electrolyte layer in contact with the second inner pump electrode is observed, a surface of the Pt particle making up the outermost surface of the second inner pump electrode is defined, on the reflection electron image, as a surface to be measured; the maximum height and the minimum height between the surface to be measured of individual ones of the Pt particles and the interface are determined from a direct distance perpendicular to the interface; and the relationships $T1-T2 \geqq 5$ and $T2/T1 \leqq 0.75$ are satisfied, wherein $T1$ (μm) is an average of the three largest values among the maximum heights arranged in a decreasing order from the largest value and $T2$ (μm) is an average of the three smallest values among the minimum heights arranged in an increasing order from the smallest value.

With such a configuration, the larger Pt particles of the Pt particles included in the second inner pump electrode can prevent the occurrence of a break in the second inner pump electrode, which may otherwise occur due to growth and coagulation of the small Pt particles. Further, the smaller Pt particles to form a coarsely textured electrode over the surface of the solid electrolyte layer, thereby enhancing a triple-layer interface ratio and electrode activity. When either $T1-T2<5$ or $T2/T1>0.75$ occurs, the surface areas of the respective exposed Pt particles become smaller, so that the triple-layer interface ratio decreases.

The expression "an interface between the second inner pump electrode and a solid electrolyte layer in contact with the second inner pump electrode" means a straight line connecting the Pt particle located closest to the solid electrolytic layer and the Pt particle located next closest to the solid electrolytic layer among the Pt particles contained in the second inner pump electrode on the reflection electron image.

In a preferred embodiment of the above second aspect, the second inner pump electrode contains 10 to 23 wt % of zirconia.

According to a third aspect, the present invention provides a method for manufacturing a gas sensor including a gas sensor element according to the above first aspect, which method comprises applying to an electrolyte layer of the gas sensor element a paste that contains, as a principal ingredient, two kinds of Pt particles having different particle sizes and whose particle size ratio as measured by sedimentation particle-size distribution ranges from 1.75 to 14.2, and which paste has a mixing ratio of large Pt particles to small Pt particles having a mass ratio of 50/50 to 10/90 (large Pt particles/small Pt particles) and sintering the paste, to thereby form the second inner pump electrode.

In a preferred embodiment of the above third aspect, the second inner pump electrode contains 10 to 28 mass % of zirconia based on a total mass of the two kinds of Pt particles.

The present invention enables shortening of a light-off time by enhancing pumping capability of the second pumping cell.

BRIEF DESCRIPTION OF THE DRAWINGS

Illustrative aspects of the invention will be described in detail with reference to the following figures in which.

DETAILED DESCRIPTION OF THE PREFERRED EMBODIMENTS

An embodiment of the present invention will next be described in reference to the drawings. However, the present invention should be construed as being limited thereto.

Figure 1:
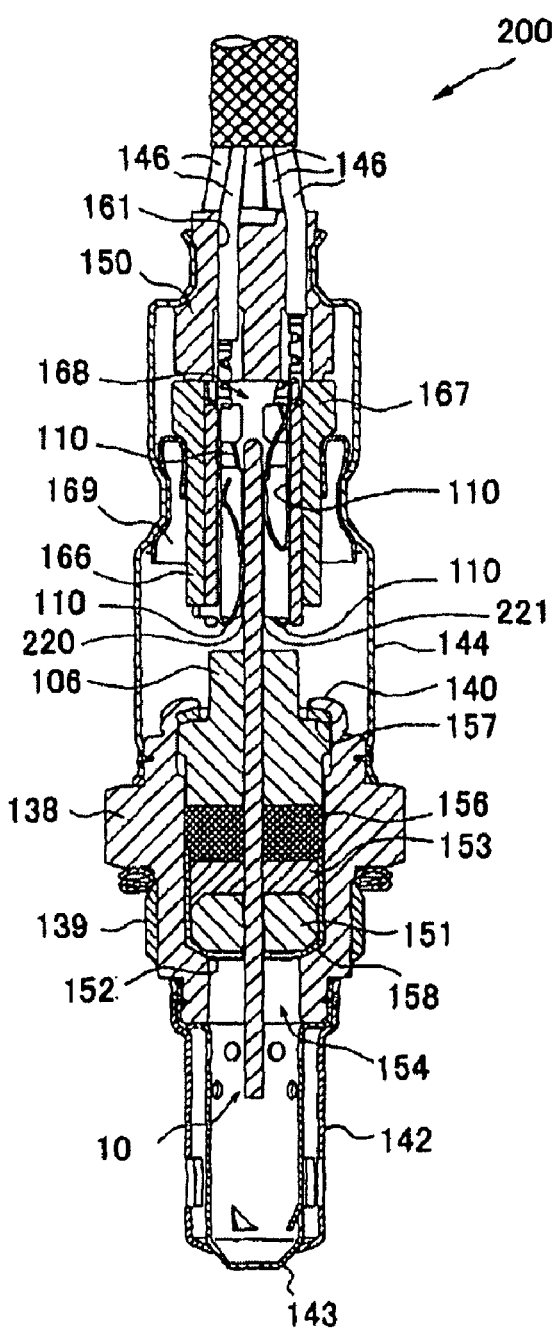
FIG. 1 is a cross-sectional view of a NOx sensor of an embodiment of the present invention taken along its longitudinal direction.

FIG. 1 is a cross-sectional view of a gas sensor (NOx sensor) 200 of an embodiment of the present invention taken along its longitudinal direction. The NOx sensor 200 has cylindrical metal shell 138 with an exterior surface on which is formed a thread 139 to be fastened to an exhaust pipe; an NOx sensor element (a gas sensor element) 10 assuming the shape of a plate extending in an axial direction (the longitudinal direction of the NOx sensor 200: the vertical direction in the drawing); a cylindrical ceramic sleeve 106 disposed so as to surround a radial circumference of the NOx sensor element 10; an insulating contact member 166 disposed in such a way that an inner wall surface defining an axially extending contact insert hole 168 surrounds a circumference of a rear end of the NOx sensor element; and six connection terminals 110 interposed between the NOx sensor element 10 and the insulating contact member 166 (two of them are illustrated in FIG. 1).

The metal shell 138 is formed into a substantially-cylindrical shape having an axially extending through hole 154 and a shoulder 152 inwardly projecting with respect to a radial direction of the through hole 154. The metal shell 138 also holds the NOx sensor element 10 within the through hole 154. A leading end of the NOx sensor element 10 protrudes from a leading end of the through hole 154, while electrode terminals 220 and 221 are disposed outside the rear end of the through hole 154. Moreover, the shoulder 152 has an inwardly-oriented tapered surface inclined with respect to a plane that is perpendicular to the axial direction.

An annular ceramic holder 151, powder-packed layers 153 and 156 (hereinafter also called talc rings 153 and 156), and the foregoing ceramic sleeve 106 are stacked in this sequence from the leading end to the rear end of the through hole 154 of the metal shell 138 so as to surround the radial circumference of the NOx sensor element 10. A crimp packing 157 is interposed between the ceramic sleeve 106 and a rear end 140 of the metal shell 138. A metal holder 158 that holds the talc ring 153 and the ceramic holder 151 and that maintains hermeticity is interposed between the ceramic holder 151 and the shoulder 152 of the metal shell 138. The rear end 140 of the metal shell 138 is crimped so as to press the ceramic sleeve 106 toward the leading end by way of the crimp packing 157.

In the meantime, as shown in FIG. 1, a double protector that covers a projecting portion of the NOx sensor element 10, that has a plurality of holes, that is made of metal (e.g., stainless steel, or the like), and that consists of an outer protector 142 and an inner protector 143, is attached to an outer periphery of the leading end side (a lower side in FIG. 1) of the metal shell 138 by means of welding, and the like.

An outer casing 144 is fixed to an outer periphery of the rear end of the metal shell 138. A grommet 150 having lead wire insert holes 161, into which six lead wires 146 (only five of them are shown in FIG. 1) are inserted to be electrically connected to the electrode terminals 220 and 221 of the NOx sensor element 10, is placed in an opening at the rear end of the outer casing 144 (an upper position in FIG. 1).

An insulation contact member 166 is placed at a rear end (an upper portion shown in FIG. 1) of the NOx sensor element 10 projecting from the rear end 140 of the metal shell 138. The insulating contact member 166 is disposed around the electrode terminals 220 and 221 formed on the surface of the rear end of the NOx sensor element 10. The insulating contact member 166 is formed into a cylindrical shape having the axially extending contact insert hole 168. And, the insulating contact member 166 has a flange 167 that projects outwards from an exterior surface in a radial direction. By virtue of the flange 167 contacting the outer casing 144 by way of a holding member 169, the insulating contact member 166 is disposed in the outer casing 144.

The structure of the NOx sensor element 10 will now be described by reference to a cross-sectional view of FIG. 2 taken along a longitudinal direction of the sensor element.

Figure 2:
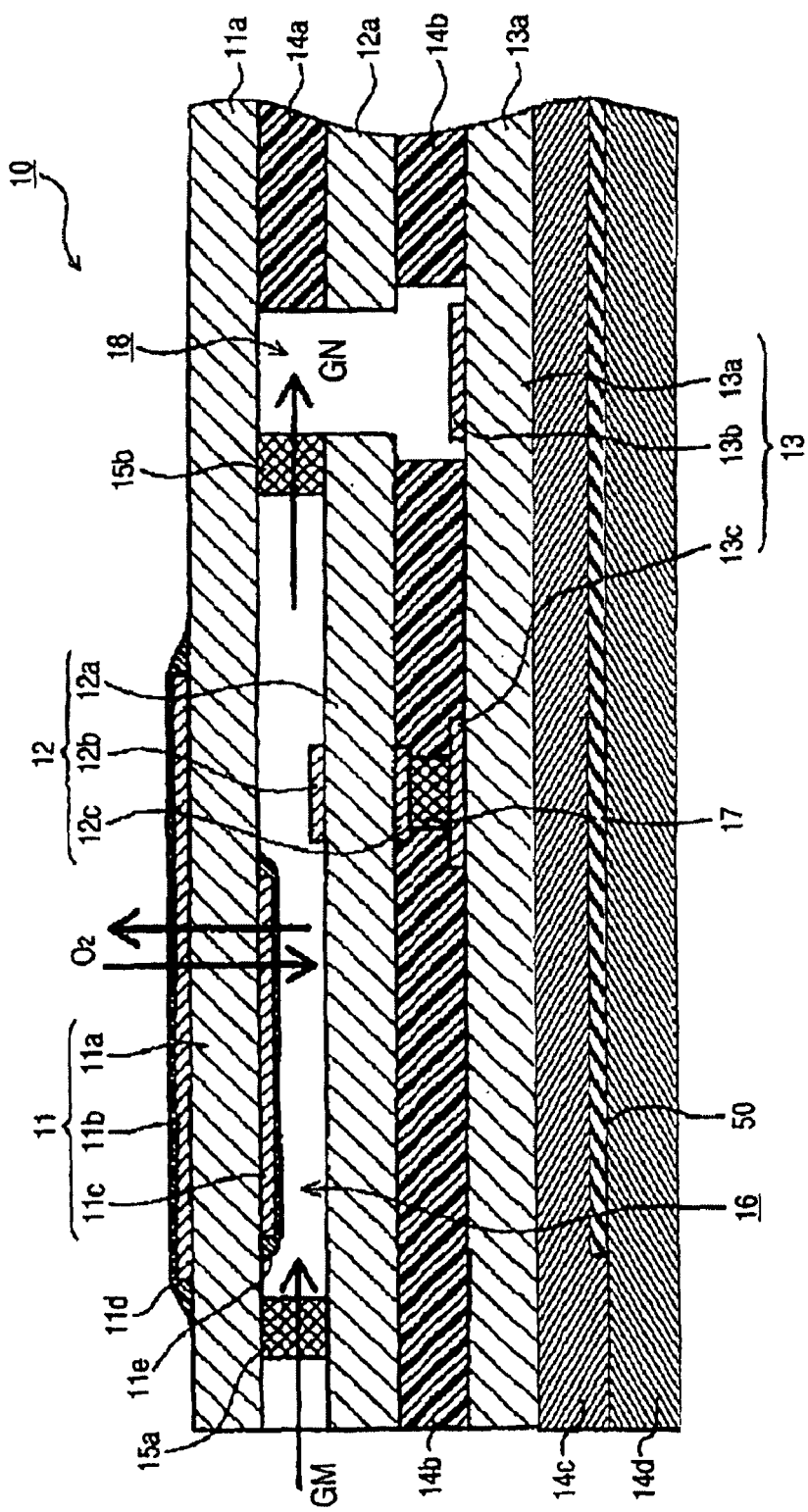
FIG. 2 is a cross-sectional view of the NOx sensor element taken along its longitudinal direction.

In FIG. 2, the NOx sensor element 10 has a structure made up of a first solid electrolyte layer 11a, an insulation layer 14a, a second solid electrolyte layer 12a, an insulation layer 14b, a third solid electrolyte layer 13a, and insulation layers 14c and 14d, all of which are stacked in this sequence. The first measurement chamber 16 is formed between the first solid electrolyte layer 11a and the second solid electrolyte layer 12a, and a gas GM to be measured is introduced from the outside by way of a first diffusive resistance element 15a disposed at the left end (an entrance) of the first measurement chamber 16.

A second diffusive resistance element 15b is disposed at an end of the first measurement chamber 16 opposite the entrance. A second measurement chamber 18 remaining in mutual communication with the first measurement chamber 16 is formed on the right side of the first measurement chamber 16 by way of the second diffusive resistance element 15b. The second measurement chamber 18 is formed between the first solid electrolyte layer 11a and the third solid electrolyte layer 13a by penetration through the second solid electrolyte layer 12a.

An elongated-plate-shaped heater 50 that extends along a longitudinal direction of the NOx sensor element 10 (a direction in which the solid electrolyte layers 11a to 13a are stacked) is embedded between the insulation layers 14c and 14d. The heater 50 is used for increasing the temperature of the gas sensor to an active temperature and enhancing conductivity of oxygen ions in the solid electrolyte layers. In this manner, operation of the sensor element is stabilized.

The insulation layers 14a to 14d are primarily made of alumina, and the first diffusive resistance element 15a and the second diffusive resistance element 15b are made of a porous substance, such as alumina. Further, the heater 50 is made of platinum, and the like.

The first pumping cell 11 has the first solid electrolyte layer 11a consisting principally of zirconia exhibiting oxygen ion conductivity, and a first inner pump electrode 11c and a first counterpart electrode (a first outer pump electrode) 11b pairing up with the first inner pump electrode 11c, wherein the first solid electrolytic layer 11a is sandwiched between the first inner pump electrode 11c and the first counterpart electrode 11a. The first inner pump electrode 11c faces the first measurement chamber 16. Each of the first inner pump electrode 11c and the first outer pump electrode 11b is made principally of platinum, and surfaces of the respective electrodes are coated with protective layers 11e and 11d that are made of a porous substance.

An oxygen concentration detection cell 12 has a second solid electrolyte layer 12a made primarily of zirconia, and a detection electrode 12b and a reference electrode 12c which are disposed such that the second solid electrolyte layer 12a is sandwiched therebetween. The detection electrode 12b is located downstream of the first inner pump electrode 11c and faces the first measurement chamber 16. Each of the detection electrode 12b and the reference electrode 12c is made primarily of platinum.

The insulation layer 14b is notched in such a way that the reference electrode 12c contacting the second solid electrolyte layer 12a is embedded in the insulation layer 14b, and the cutout is filled with a porous substance, to thus create a reference oxygen chamber 17. In operation, an extremely-small current of given value is previously caused to flow into the oxygen concentration detection cell 12, thereby supplying oxygen to the reference oxygen chamber 17 from the first measurement chamber 16 and establishing an oxygen reference concentration.

The second pumping cell 13 has a third solid electrolyte layer 13a made primarily of zirconia, and a second inner pump electrode 13b and a second counterpart electrode (a second counterpart pump electrode 13c) pairing up with the second inner pump electrode 13b, which are disposed at areas on the surface of the third solid electrolyte layer 13a facing the second measurement chamber 18. Each of the second inner pump electrode 13b and the second counterpart pump electrode 13c is made primarily of platinum.

The second counterpart pump electrode 13c is disposed in the cutout of the insulation layer 14b located above the third solid electrolyte layer 13a; opposes the reference electrode 12c; and faces the reference oxygen chamber 17.

An example operation of the NOx sensor element 10 will now be described. First, when power is supplied from an external power supply by starting the engine, the heater 50 operates by way of a predetermined control circuit, thereby heating the first pumping cell 11, the oxygen concentration detection cell 12, and the second pumping cell 13 to an activation temperature. When the respective cells 11 to 13 are heated to the activation temperature, the first pumping cell 11 pumps, from the first inner pump electrode 11c toward the first counterpart electrode 11b excess oxygen in the gas GM to be measured (an exhaust gas) which has been introduced into the first measurement chamber 16.

At this time, the concentration of oxygen in the first measurement chamber 16 corresponds to a voltage Vs (a terminal-to-terminal voltage) across the electrodes of the oxygen concentration detection cell 12. Therefore, an electrode-to-electrode voltage (a terminal-to-terminal voltage) Vp1 of the first pumping cell 11 is controlled in such a way that the electrode-to-electrode voltage Vs reaches a constant voltage V1 (e.g., 425 mV), thereby adjusting the concentration of oxygen in the first measurement chamber 16 to an extent that NOx is not decomposed.

The gas GN to be measured having an adjusted oxygen concentration flows toward the second measurement chamber 18. A given voltage Vp2 (a voltage that is higher than a value of a control voltage for the oxygen concentration detection cell 12; for instance, 450 mV) at which NOx gas in the gas GN to be measured is decomposed into oxygen and $N_2$ gas is applied as an electrode-to-electrode voltage (a terminal-to-terminal voltage) Vp2 of the second pumping cell 13, whereupon NOx is decomposed into nitrogen and oxygen. A second pump current Ip2 flows through the second pumping cell 13 in such a way that oxygen resulting from decomposition of NOx is pumped out of the second measurement chamber 18. Since a linear relationship exists between the second pump current Ip2 and the concentration of NOx at this time, the concentration of NOx in the gas to be measured can be detected by detecting Ip2.

The second inner pump electrode 13b will now be described. The second inner pump electrode 13b is made primarily of two types of Pt particles of differing particle size at which a particle size ratio, which has been measured in terms of a sedimentation particle-size distribution, ranges from 1.75 to 14.2. Further, a mixing ratio between large Pt particles and small Pt particles ranges from 10/90 to 50/50 (large Pt particles/small Pt particles) in terms of a mass ratio. The second inner pump electrode 13b is made by applying a mixture of such Pt particles in the form of a paste along with a binder, a component of the solid electrolyte layer, a solvent, and the like, and sintering the mixture at a temperature of about 800° C. or higher. However, the production method is not limited to that mentioned above.

When the second inner pump electrode 13b is made of a mixture of such Pt particles, a resistance value of the second pumping cell 13 ranging from 10 kHz to 1 Hz becomes 150Ω or less, whereby the light-off time is shortened. The reason for this is that the small Pt particles form a coarsely textured electrode over the surface of the solid electrolyte layer, to thus enhance a triple-layer interface ratio and increase electrode activity. Further, mixing of large Pt particles enables the prevention of a break in the second inner pump electrode 13b, which would otherwise be attributable to growth and coagulation of the small Pt particles.

The particle size ratio between the two kinds of Pt particles having different particle sizes of this invention ranges from 1.75 to 14.2. When the particle size ratio is less than 1.75, the light-off time is not shortened. A conceivable reason for this is that the large Pt particles cannot inhibit growth of the small Pt particles because of a small difference in the particle sizes of the two kinds of Pt particles, which in turn causes a break in the second inner pump electrode 13b. On the other hand, even when the particle size ratio exceeds 14.2, the light-off time is not shortened. A conceivable reason for this is that growth and coagulation of the small Pt particles are accelerated because of a large difference in particle size of the two kinds of Pt particles, which in turn makes the electrode susceptible to breaking.

The particle size measured in terms of a sedimentation particle-size distribution means an average particle size that are determined by utilizing a phenomenon in which the observed sedimentation speed depends on particle size when fine particles settle in a stationary fluid. The sedimentation particle-size distribution can be measured by use of, for instance, a centrifugal sedimentation particle-size distribution measurement apparatus (SA-CP3) manufactured by the Shimadzu Corporation.

A mixing ratio of Pt particles contained in the second inner pump electrode 13b ranges from 10/90 to 50/50 (large Pt particles/small Pt particles) in terms of a mass ratio. When the mass ratio is less than 10/90, the large Pt particles become small in quantity, and a break can occur in the second inner pump electrode 13b as a result of growth and coagulation of the small Pt particles. On the other hand, when the mass ratio exceeds 50/50, the small Pt particles become small in quantity. Hence, it becomes difficult to form a coarsely textured electrode over the surface of the solid electrolyte layer, which in turn does not enhance the triple-layer interface ratio and electrode activity.

The Pt particles grow from a powdery after having been formed the second inner pump electrode 13b. Hence, even when the electrode is observed, it is difficult to ascertain a particle size difference among the Pt particles. However, when the second inner pump electrode is made of the above Pt particles, the sensor element exhibits a characteristic of a 10 kHz-1 Hz resistance value across the second pumping cell 13 of 150Ω or less at 600° C.

The present inventors experimentally determined that the light-off time is shortened to one-half or more of the light-off time of a related-art NOx sensor by setting the 10 kH-1 Hz resistance value achieved across the second pumping cell 13 to 150Ω or less. The 10 kHz-1 Hz resistance value is obtained by measuring AC impedance between one pair of electrodes of the second pumping cell 13 at a single frequency ranging from 0 to 100 kHz and by drawing a measurement result by means of a Cole-Cole plot (plotting a measurement result on a complex impedance plane).

Figure 3:
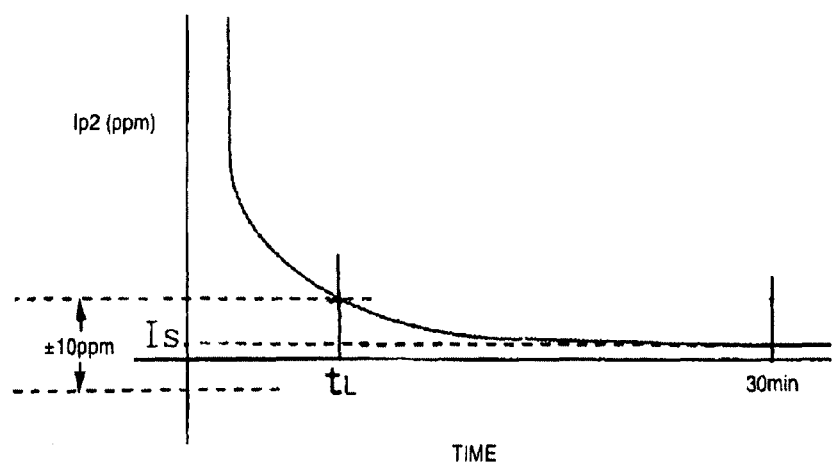
FIG. 3 is a view showing a method for measuring a light-off time.

The light-off time is a period from when start-up control of the sensor begins until the concentration of $O_2$ in the second measurement chamber (the second pump current) is reduced to a given level by means of pumping. Several methods are available for measuring the light-off time. For instance, a method shown in FIG. 3 is provided. First, a gas sensor is placed at room temperature in the atmosphere, and a change in sensor output value pertaining to the second pump current Ip2 with time since initiation of energization of the heater is measured. An Ip2 achieved after a lapse of 30 minutes since initiation of heater energization is deemed to be a saturated value Is, and a time tL at which Ip2 assumes a value of Is±10 ppm is taken as the light-off time. Ip2 usually assumes a large value at the time that heater energization is initiated. A time at which Ip2 assumes a value that is higher than Is by 10 ppm is taken as tL.

An area of the second inner pump electrode 13b that is exposed in the second measurement chamber and that reacts as an electrode is made of the Pt particles mentioned above. It is preferable to use an ordinary Pt material for the other lead portion.

When the second inner pump electrode 13b contains 10 to 28 mass % of zirconia based on a total mass of the Pt particles of two kinds, adhesion of the electrode to the solid electrolyte is preferably enhanced. Zirconia is the principal component of the solid electrolyte layer. When the zirconia content is less than 10 mass percent, enhancement of electrolyte adhesion is small, and the triple-layer interface ratio trends downward. When the zirconia content exceeds 28 mass %, adhesion of the electrode increases. However, a break can occur in the Pt electrode, and the triple-layer interface ratio trends downward.

Moreover, the second inner pump electrode 13b is preferably doped with, as a component for enhancing the activity of the electrode, one or more of Rh, Pd, Ru and Ir.

An average thickness of the second inner pump electrode 13b is preferably 15 µm or less, and the minimum thickness of the same is preferably 11 µm or less. The reason for this is that, under a situation where a triple-layer interface is generated, oxygen can migrate to the solid electrode layer immediately after being decomposed on the electrode as the second inner pump electrode 13b is made thinner, thereby enhancing pumping capability. A preferred minimum thickness of the second inner pump electrode 13b is 4 µm or more. Thus, oxygen in the second measurement chamber 18 can be sufficiently pumped out without imparting a break in the second inner pump electrode 13b.

In measuring the average thickness and the minimum thickness of the second inner pump electrode, a surface roughness measuring instrument defined in JIS B0651 (2007 Year Version) (3.2 a contact surface roughness measuring instrument) is used to perform a sweeping operation along, for instance, a longitudinal direction of FIG. 2, from the third solid electrolyte layer 13a (exposed on the left side) beyond the second inner pump electrode 13b so as to reach the third solid electrolyte layer 13a (exposed on the right side) by crossing the second inner pump electrode 13b, thereby identifying the shape of the inner second pump electrode.

The average thickness of the second inner pump electrode can be determined by Rz (entire)–Rc (an electrode). Rz (entire) designates the maximum height achieved in the entire sweep range, and Rc (an electrode) designates an average height achieved within the range over which the second inner pump electrode 13b is subjected to sweeping. The minimum thickness of the second inner pump electrode can be determined by Rz (entire) to Rz (an electrode). Rz (an electrode) designates the maximum height achieved within the range over which the second inner pump electrode 13b is subjected to sweeping.

Of the Pt particles making up the second inner pump electrode 13b, the outermost surface of the second inner pump electrode 13b is defined as a surface to be measured. Surfaces to be measured of the respective Pt particles and the maximum and minimum heights located at an interface between the second inner pump electrode 13b and the third solid electrolyte layer 13a are determined with reference to a direct distance N achieved in a direction perpendicular to the interface. When an average of three values of the greatest three values of the thus-determined maximum heights is taken as T1 (µm) and when an average of the three minimum values of the minimum heights is taken as T2 (µm), it is preferable to achieve a relationship of T1−T2≧5 and T2/T1≦0.75. By adopting such a configuration, large Pt particles of the Pt particles contained in the second inner pump electrode 13b prevent the occurrence of a break in an electrode, which may otherwise result due to growth and coagulation of the small Pt particles. Moreover, the small Pt particles form a coarsely textured electrode over the surface of the third solid electrolytic layer 13a, whereby a triple-layer interface ratio and electrode activity are enhanced.

T1 and T2 can be specified by observing, among the cut planes acquired by cutting the gas sensor element 10 in a stacking direction, a reflection electron image (SEM) including the second inner pump electrode 13b and the interface L between the second inner pump electrode 13b and the third solid electrolyte layer 13a.

Figure 7:
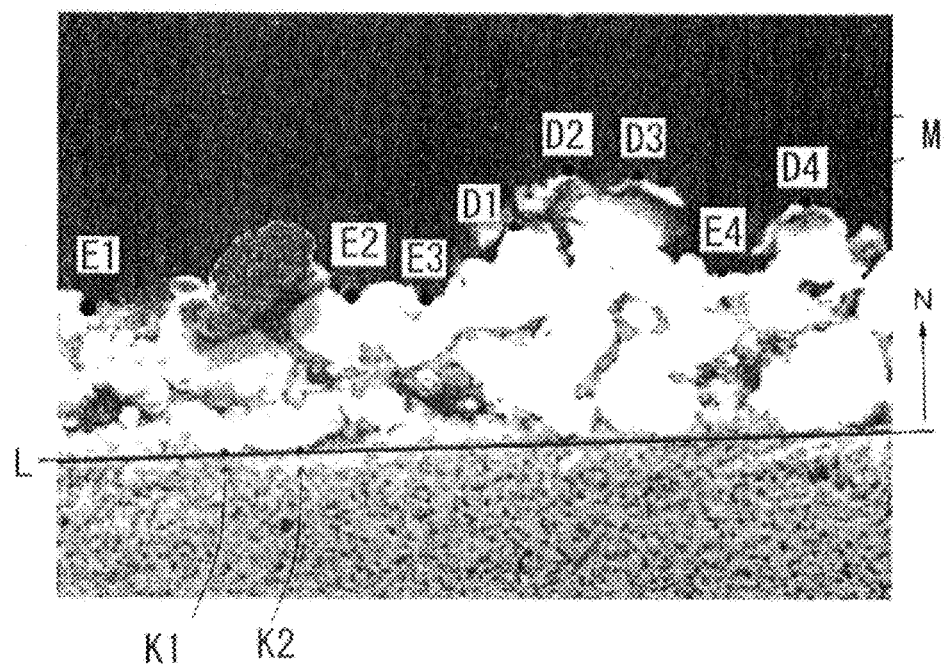
FIG. 7 is a descriptive view for computing T1 and T2 from a reflection electron image.

Specifically, the interface L is first defined in the reflection electron image, such as that shown in FIG. 7. The interface L is specified as a straight line that connects the Pt particle (K1) located closest to the third solid electrolyte layer 13a to the Pt particle (K2) located next closest to the third solid electrolyte layer 13a among the Pt particles in the second inner pump electrode 13b.

The outermost surfaces of the Pt particles making up the second inner pump electrode 13b are defined as surfaces M to be measured. The maximum height and the minimum height achieved between the surface M to be measured of each Pt particle and the interface L are determined with reference to a direct distance achieved in a direction perpendicular to the interface L. FIG. 7 shows only the maximum heights D1, D2, D3 and D4 and the minimum heights E1, E2, E3 and E4; however, other maximum and minimum heights are also determined.

An average of three values (D2, D3 and D4 in FIG. 7) that are in a decreasing order form the largest value of the maximum heights is taken as T1. An average of three values (E1, E2 and E3 in FIG. 7) that are in an increasing order form the smallest value of the minimum heights is taken as T2.

T1 and T2 are measured by observing a cutting plane that includes the interface between the second inner pump electrode 13b and the third solid electrolytic layer 13a and that is cut along the stacking direction of the gas sensor, by means of the reflection electron image of the scanning electron microscope (SEM). The requirement for a measurement range of the reflection electron image is 1000× magnification or more. The reflection electron image can usually be observed in a field of view of about 70×50 µm.

Moreover, the reason for acquiring a relationship of T1−T2≧5 (µm) is that as the difference between T1 and T2 comes to an absolute value of 5 µm or more, the large Pt particles are situated closer to the surface of the second inner pump electrode 13b than are the small Pt particles, and irregularities of the outermost surface become greater.

Further, when T2/T1≦0.75 is achieved, T1 outstandingly exceeds one-fourth of the length of T2, and the irregularities of the outermost surface of the second inner pump electrode 13b become great.

The greater irregularities are considered to show the extent to which the large Pt particles are heavily distributed outside of the second inner pump electrode 13b and further, that the small Pt particles are correspondingly heavily distributed over the surface of the third solid electrolyte layer 13a.

Normally, in the gas sensor, the pumping capability of the second pumping cell 13 is low, and the electric current flowing through the first pumping cell 11 is 20 times or greater than the electric current flowing through the second pumping cell 13.

When the lower limit of oxygen concentration of the first measurement chamber 16 is 1%, the minimum value of the first pump current Ip1 is 0.125 mA (=125 µA). At this time, provided that the upper limit of the NOx concentration in the second measurement chamber 18 is 2000 ppm, the second pump current Ip2 is on the order of 6 µA.

As shown in FIG. 2, when the second inner pump electrode 13b and the counterpart second pump electrode 13c of the second pumping cell 13 are on the same surface side of the third solid electrolyte layer 13a (i.e., an upper surface in the drawing), the cell resistance becomes higher than that achieved in the case where the inner pump electrode 13b and the second counterpart electrode 13c oppose each other, which deteriorates pumping capability. Hence, the present invention is effective.

The present invention is specifically described by reference to the following Examples. However, as a matter of course, the present invention is not limited thereto.

Example 1

The NOx sensor described in connection with the embodiment shown in FIGS. 1 and 2 was manufactured in accordance with a related-art method. The second inner pump electrode 13a was formed by applying any of Pt pastes described below over the third solid electrolyte layer 13a by means of screen printing, to thus stack the paste layer over another layer, and sintering the entirety (e.g., at 1500° C. for one hour).

Pt pastes were prepared by mixing at the ratios shown in Table 1 a Pt powder (including large Pt particles) having an average particle size of 7.9 μm with a Pt powder (small Pt particles) having an average particle size of 4.5 μm. Moreover, zirconia and an organic binder were admixed with all of the Pt powders at the ratios shown in Table 1, and a solvent and a plasticizer were added as appropriate to the mixtures, to thus prepare the Pt pastes.

The impedance between the second inner pump electrode 13b and the counterpart second pump electrode 13c in the second pumping cell 13 of the thus-obtained NOx sensor was measured with an impedance analyzer (Model 1260 manufactured by Solartron Co., Ltd.). The sensor was controlled to a control temperature of 600° C. by means of the heater at the time of measurement. An applied voltage was set to an a.c. (AC) voltage of 200 mV, and a sweep was performed at a measurement frequency domain from 10 k to 1 Hz.

As described by reference to FIG. 3, in relation to the light-off time, the gas sensor was placed in an atmosphere of normal temperature, and hourly changes in the sensor output value pertaining to the second pump current Ip2 were measured from initiation of energization of the heater. The current Ip2 achieved after elapse of 30 minutes from initiation of energization of the heater is deemed to be a saturated value Is, and a time tL at which Ip2 reaches a value of Is+10 ppm was taken as the light-off time. The heater was controlled such that the sensor temperature reached 680° C.

TABLE 1

| | Component of paste used for making second inner pump electrode | | | | Thickness of second inner pump electrode | | Evaluation | | | |
|---|---|---|---|---|---|---|---|---|---|---|
| | Pt particles having large particle sizes (wt %) (average particle size of 7.9 μm) | Pt particles having small particle sizes (wt %) (average particle size of 4.5 μm) | Zirconia (wt % based on the total amount of Pt) | Organic binder (wt % based on the total amount of Pt) | Minimum thickness (μm) | Average thickness (μm) | 10 kHz-to-1 Hz resistance (Ω) | Light-off time | Adhesion | Breakage |
| Comparative example 1 | 0 | 100 | 10 | 14 | 3 | 11 | 158 | 45 | — | — |
| Comparative example 2 | 0 | 100 | 28 | 14 | 3 | 12 | 170 | 48 | — | — |
| Comparative example 3 | 0 | 100 | 28 | 5 | 2 | 11 | 210 | 51 | — | — |
| First example of the invention | 10 | 90 | 7 | 14 | 5 | 12 | 35 | 37 | Δ | ○ |
| Second example of the invention | 50 | 50 | 7 | 14 | 11 | 15 | 145 | 39 | Δ | ○ |
| Third example of the invention | 10 | 90 | 10 | 14 | 5 | 12 | 8 | 37 | ○ | ○ |
| Fourth example of the invention | 10 | 90 | 28 | 14 | 4 | 11 | 20 | 38 | ○ | ○ |
| Fifth example of the invention | 10 | 90 | 28 | 5 | 7 | 12 | 24 | 37 | ○ | ○ |
| Sixth example of the invention | 26 | 74 | 10 | 14 | 9 | 12 | 50 | 36 | ○ | ○ |
| Seventh example of the invention | 26 | 74 | 28 | 14 | 11 | 13 | 80 | 39 | ○ | ○ |
| Eighth example of the invention | 26 | 74 | 28 | 5 | 9 | 13 | 84 | 38 | ○ | ○ |
| Ninth example of the invention | 50 | 50 | 10 | 14 | 11 | 15 | 115 | 37 | ○ | ○ |
| Tenth example of the invention | 50 | 50 | 14 | 10 | 11 | 15 | 120 | 38 | ○ | ○ |
| Eleventh example of the invention | 50 | 50 | 28 | 14 | 11 | 14 | 132 | 39 | ○ | ○ |
| Twelfth example of the invention | 50 | 50 | 28 | 5 | 10 | 15 | 150 | 38 | ○ | ○ |
| Thirteenth example of the invention | 50 | 50 | 32 | 14 | 11 | 15 | 145 | 39 | ○ | Δ |

TABLE 1-continued

| | Component of paste used for making second inner pump electrode | | | | Thickness of second inner pump electrode | | Evaluation | | | |
|---|---|---|---|---|---|---|---|---|---|---|
| | Pt particles having large particle sizes (wt %) (average particle size of 7.9 μm) | Pt particles having small particle sizes (wt %) (average particle size of 4.5 μm) | Zirconia (wt % based on the total amount of Pt) | Organic binder (wt % based on the total amount of Pt) | Minimum thickness (μm) | Average thickness (μm) | 10 kHz-to-1 Hz resistance (Ω) | Light-off time | Adhesion | Breakage |
| Fourteenth example of the invention | 10 | 90 | 32 | 14 | 4 | 11 | 37 | 37 | ○ | Δ |
| Comparative example 4 | 74 | 26 | 10 | 14 | 12 | 15 | 230 | 60 | — | — |
| Comparative example 5 | 74 | 26 | 28 | 14 | 13 | 16 | 250 | 63 | — | — |
| Comparative example 6 | 74 | 26 | 22 | 7 | 12 | 15 | 330 | 81 | — | — |
| Comparative example 7 | 74 | 26 | 28 | 5 | 11 | 17 | 360 | 88 | — | — |
| Comparative example 8 | 100 | 0 | 10 | 14 | 13 | 18 | 480 | 125 | — | — |
| Comparative example 9 | 100 | 0 | 28 | 14 | 14 | 19 | 500 | 140 | — | — |
| Comparative example 10 | 100 | 0 | 28 | 5 | 12 | 18 | 650 | 220 | — | — |

Figure 4:
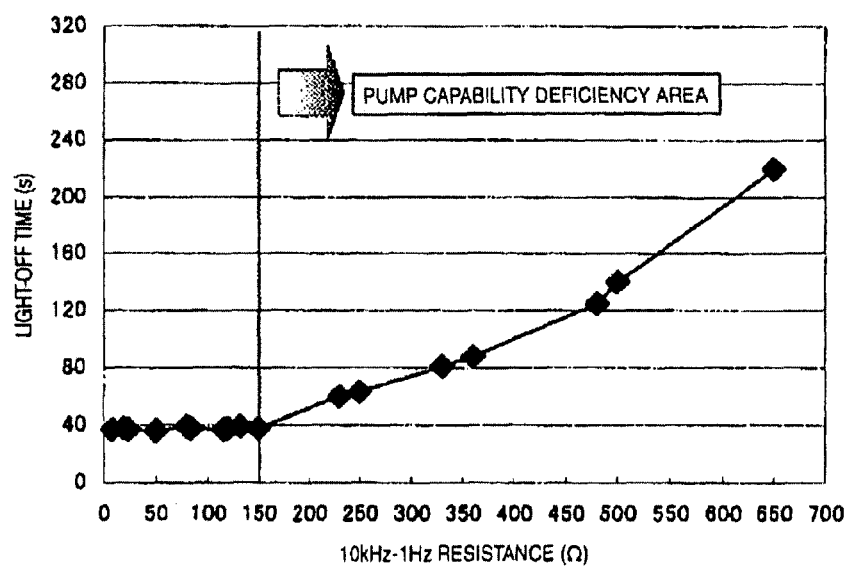
FIG. 4 is a view showing a relationship between a 10 kHz-1 Hz resistance value achieved across a second pumping cell and the light-off time.

The results thus obtained are shown in Table 1 and FIG. 4. In the case of the first to fourteenth examples of the invention in which the mass ratio falls within a range of 10/90 to 50/50 (large Pt particles/small Pt particles), the light-off time was 40 seconds or less in a10 cases, and the 10 kHz-1 Hz resistance value achieved across the second pumping cell was 150Ω or less.

On the other hand, in the case of the first through third comparative examples in which only small Pt particles were employed and the fourth to tenth comparative cases in which the ratio of the large Pt particles exceeded 50 mass %, the light-off time exceeded 40 seconds. The 10 kHz-1 Hz resistance value achieved across the second pumping cell at this time also exceeded 150Ω.

Thus, according to the invention, the mixing ratio between the Pt particles is set to 10/90 to 50/50 and the 10 kHz-1 Hz resistance value achieved across the second pumping cell is set to 150Ω or less. In the first example, the particle size ratio between the Pt particles was 1.75.

Figure 8:
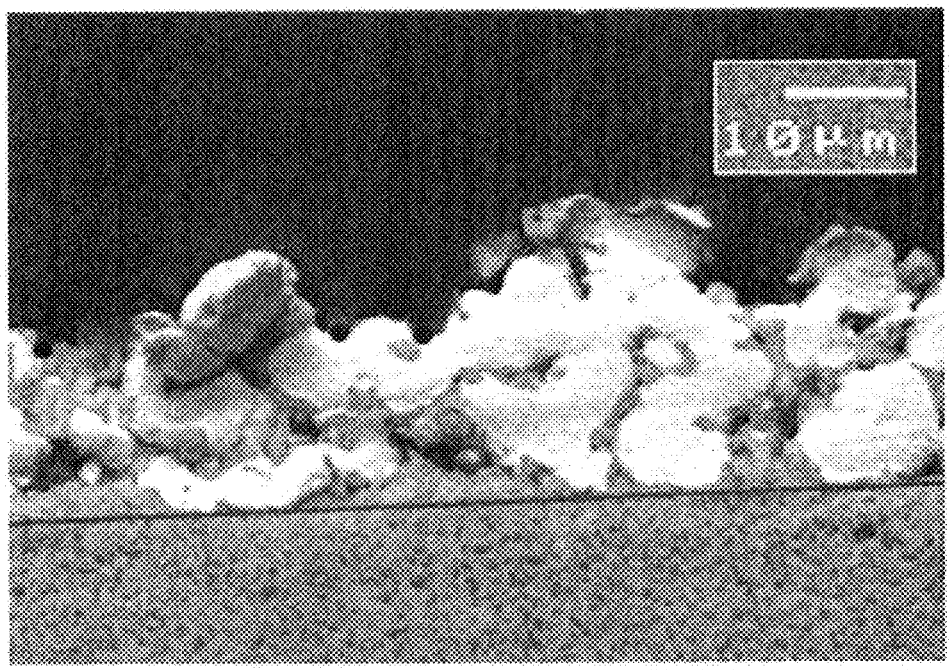
FIG. 8 is a reflection electron image of a sample of the tenth example of the invention.
Figure 9:
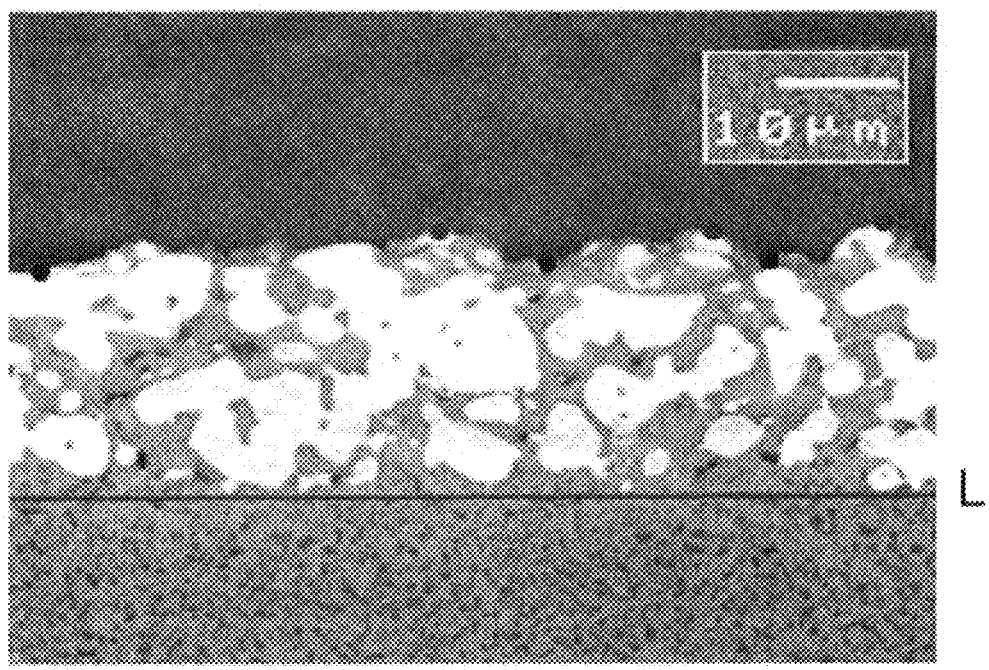
FIG. 9 is a reflection electron image of a sample of the sixth comparative example.

In a reflection electron image (SEM) observed in connection with the tenth example of the invention (see FIG. 8), T1−T2=8.9 and T2/T1=0.586 were acquired. On the other hand, in a reflection electron image (SEM) observed in connection with the sixth comparative example (see FIG. 9), T1−T2=2.4 and T2/T1=0.879 were acquired.

Adhesion and breakage of the second inner pump electrode was evaluated in connection with the first through fourteenth examples of the invention, as follows.

Adhesion of the electrode was evaluated in compliance with JIS H8504 (2007 Year Version). First, an adhesive tape with an area of 10 mm not to be affixed was pasted to a possible-flat surface of the second inner pump electrode 13b, and the tape was continually, strongly pressed with a finger for about 10 seconds while attention was paid to prevent generation of bubbles. Next, a tape piece, which was left unaffixed, was strongly pulled so as to become perpendicular with respect to the electrode surface; the tape was momentarily exfoliated; and the of the affixing surface was visually observed. If adhesion of an electrode material to the affixing surface cannot be visually ascertained, adhesion is determined to be superior (○). When adhesion of the electrode material can be visually observed, adhesion is determined to be inferior to some extent (Δ). Even when the electrode is determined to be inferior to some extent (Δ) by evaluation, no practical problem arises.

A determination is made as to whether or not a break exists in an electrode at room temperature by means of a four-terminal method and by use of a tester. When a break exists in one or more (10% or more) of ten sensor samples, the electrode(s) is determined to have a break (Δ). Even when the electrode is determined to be inferior to some extent (Δ) by evaluation, no practical problem arises.

In the case of the first and second examples of the invention, the content of zirconia based on the total Pt content in the second inner pump electrode 13b came to less than 10 mass %, and the electrode adhesion became worse than the other examples of the invention. In the meantime, in the case of the thirteenth and fourteenth examples of the invention, the content of zirconia based on the total Pt content in the second inner pump electrode 13b exceeded 28 mass %, and a break occurred in the electrode.

Example 2

NOx sensors were produced through procedures common to Example 1. The second inner pump electrode 13b was produced by applying the respective Pt pastes shown in Table 2 over the third solid electrolyte layer 13a by means of screen printing, to thus stack the electrolyte layer over another layer, and sintering the entirety (for example, at 1500° C. for one hour).

In Example 2, Pt particles each were mixed at a constant ratio of 50/50, as a mass ratio, (large Pt particles A/small Pt particles B).

TABLE 2

| | Pt particles A having a large particle size (average particle size, μm) | Pt particles B having a small particle size (average particle size, μm) | Particle size ratio (Pt particles A/Pt particles B) | Zirconia (wt % based on the total amount of Pt) | Organic binder (wt % based on the total amount of Pt) | Evaluation | |
|---|---|---|---|---|---|---|---|
| | | | | | | 10 kHz-to-1 Hz resistance (Ω) | Light-off time |
| Comparative example 11 | 12.8 | 0.6 | 21.30 | 28% | 5% | 235 | 62 |
| Twenty-first example of the invention | 12.8 | 0.9 | 14.20 | 28% | 5% | 145 | 38 |
| Twenty-second example of the invention | 7.9 | 0.9 | 8.78 | 28% | 5% | 125 | 37 |
| Twenty-third example of the invention | 12.8 | 4.5 | 2.84 | 28% | 5% | 130 | 39 |
| Twenty-fourth example of the invention | 7.9 | 4.5 | 1.75 | 28% | 5% | 150 | 38 |
| Comparative example 12 | 7.9 | 7.9 | 1.00 | 28% | 5% | 265 | 68 |

Figure 5:
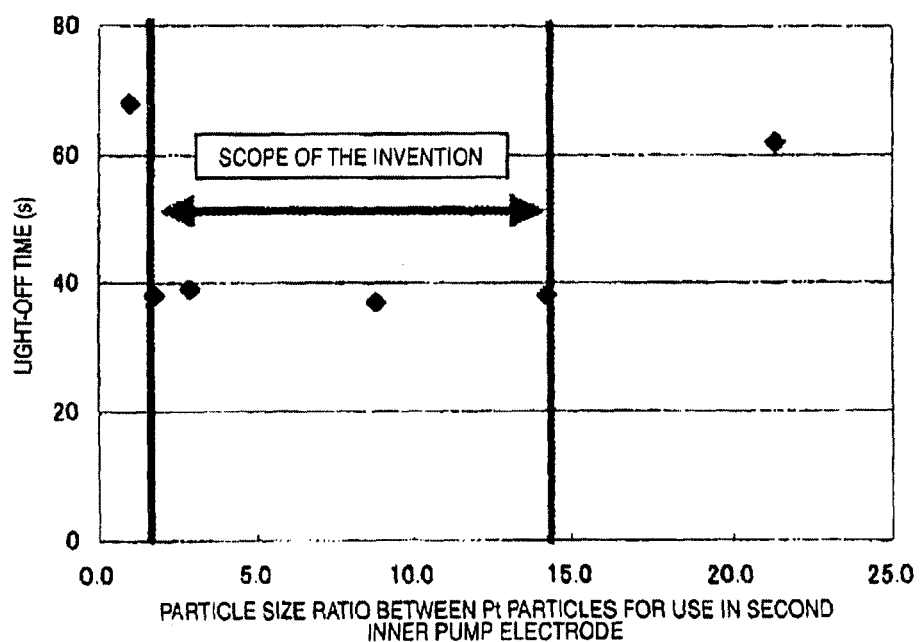
FIG. 5 is a view showing a relationship between a particle size ratio of Pt particles used in a second inner pump electrode and the light-off time.
Figure 6:
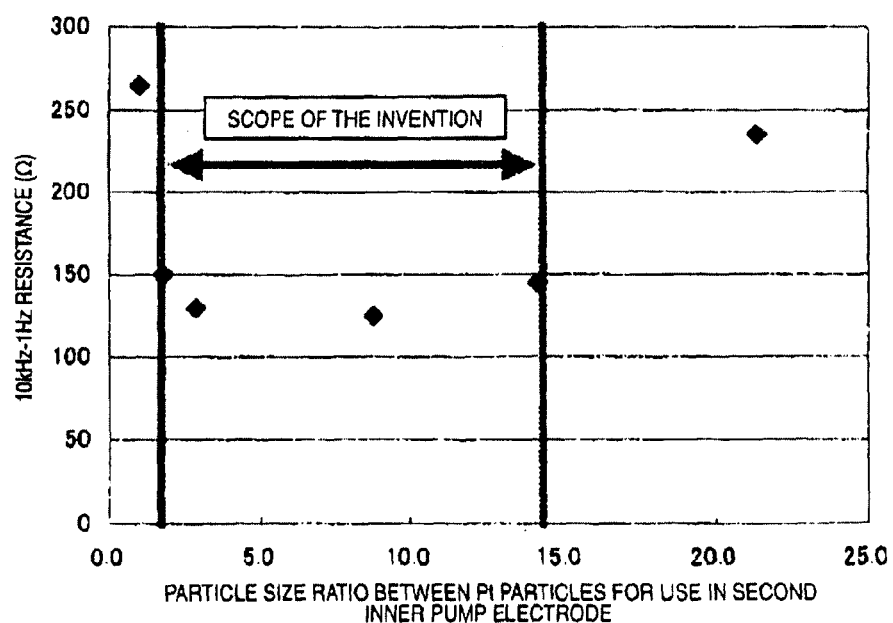
FIG. 6 is a view showing a relationship between a particle size ratio of Pt particles used in the second inner pump electrode and the 10 kHz-1 Hz resistance value achieved across the second pumping cell.

The results thus obtained are shown in Table 2, FIG. 5 and FIG. 6. In the case of the twenty-first to twenty-fourth examples of the invention in which the particle size ratio among the Pt particles ranged from 1.75 to 14.2, the light-off time was 40 seconds or less in all cases. The 10 kHz-1 Hz resistance value achieved across the second pumping cell was 150Ω or less at this time.

On the other hand, in the case of the eleventh comparative example in which a particle size ratio among the Pt particles exceeded 14.2 and the twelfth comparative example in which a particle size ratio among the Pt particles was less than 1.75, the light-off time exceeded 40 seconds in both cases. The 10 kHz-1 Hz resistance value achieved across the second pumping cell exceeded 150Ω at this time.

From the above, in accordance with the invention, a particle size ratio among the Pt particles is set to 1.75 to 14.2 and the 10 kHz-1 Hz resistance value achieved across the second pumping cell is set to 150Ω or less.

The present invention is not limited to the above embodiment, and, needless to say, the present invention covers various modifications and equivalents falling within the spirit and scope of the claims appended hereto. For instance, the planar shape of the heater is not limited to that mentioned above.

In the embodiment, the solid electrolyte layer making up the NOx sensor element is embodied in the form of a triple-layer; however, the solid electrolyte layer may also be embodied as a double layer. The structure of a NOx sensor element having a double solid electrolyte layer is described; for instance, in JP-A-2004-354400 (FIG. 3).

The present invention can be applied to a gas sensor for detecting the concentration of NOx gas in the exhaust gas of an automobile or various engines or the concentration of NOx gas in a combustion gas of a boiler, and the like, as well as to an oxygen sensor, such as a wide range air-fuel ratio sensor. However, the present invention is not limited to such applications. For instance, the present invention can also be applied to a gas sensor having a gas sensor element for measuring the concentration of a gas other than an NOx gas (e.g., $COx$, $H_2O$, HC and the like).

According to a first illustrative aspect of the exemplary embodiment, the second inner pump electrode is made of a material that contains, as a principal ingredient, two kinds of Pt particles having different particle sizes and whose particle size ratio as measured by a sedimentation particle-size distribution ranges from 1.75 to 14.2, and which has a mixing ratio of large Pt particles to small Pt particles assuming a mass ratio of 10/90 to 50/50 (large Pt particles/small Pt particles); and a 10 kHz-1 Hz resistance value achieved across the second pumping cell at 600° C. is 150Ω or less.

With such a configuration, large Pt particles of the Pt particles included in the second inner pump electrode prevent the occurrence of a break in an electrode, which might otherwise occur due to growth and coagulation of the small Pt particles. Further, the small Pt particles form a coarsely textured electrode over the surface of the solid electrolyte layer, thereby enhancing a triple-layer interface ratio and electrode activity. Consequently, a 10 kHz-1 Hz resistance value achieved across the second pumping cell becomes 150Ω or less, and the light-off time is shortened as compared with that achieved by a related-art NOx sensor.

According to another illustrative aspect of the exemplary embodiment, an average thickness of the second inner pump electrode is 15 μm or less, and the minimum thickness of the same ranges from 4 μm to 11 μm.

With such a configuration, oxygen can migrate to the solid electrolyte layer immediately after oxygen is decomposed on the electrode, so long as the second inner pump electrode is thinly made to an extent that no break occurs in the electrode under the situation where a triple-layer interface is created. Hence, pumping capability is enhanced.

According to yet another illustrative aspect of the exemplary embodiment, the second inner pump electrode is made of an aggregate that contains Pt as a principal ingredient consisting of a plurality of Pt particles including larger Pt particles and smaller Pt particles, in a cutting plane of the gas sensor element taken along its stacking direction, when a reflection electron image including an interface between the second inner pump electrode and a solid electrolyte layer in contact with the second inner pump electrode is observed, a surface of the Pt particle making up the outermost surface of the second inner pump electrode is defined, on the reflection electron image, as a surface to be measured, the maximum height and the minimum height between the surface to be measured of individual ones of the Pt particles and the interface are determined from a direct distance perpendicular to the interface, and the relationships $T1-T2 \geq 5$ and $T2/T1 \leq 0.75$ are satisfied, wherein T1 (μm) is an average of the three largest values among the maximum heights arranged in a decreasing order from the largest value and T1(μm) is an average of the three smallest values among the minimum heights arranged in an increasing order from the smallest value.

With such a configuration, large Pt particles of the Pt particles included in the second inner pump electrode prevent the occurrence of a break in an electrode, which may otherwise occur due to growth and coagulation of the small Pt particles. Also, the small Pt particles form a coarsely textured electrode over the surface of the solid electrolytic layer, thereby enhancing a triple-layer interface ratio and electrode activity. When either $T1-T2<5$ or $T2/T1>0.75$ occurs, the surface areas of exposed Pt particles become smaller, so that the triple-layer interface ratio decreases.

According to yet another illustrative aspect of the exemplary embodiment, the second inner pump electrode contains 10 to 28 wt % of zirconia.

With such a configuration, zirconia that is the principal ingredient of the solid electrolyte layer simultaneously fulfills an enhanced triple-layer interface ratio in the electrode and enhanced electrode adhesion. It is preferable to use zirconia partially stabilized by yttria, and the like. As a result of use of such a partially-stabilized zirconia, zirconia becomes less likely to be embedded in a space within the electrode. The triple-layer interface thus exposed in the space can sufficiently function, whereby electrode activity is enhanced. Use of zirconia whose particle size ranges from 0.2 to 2 μm is also preferable. As a result, zirconia becomes less likely to be embedded in a space within the electrode, and the triple-layer interface exposed in the space can function, whereby electrode activity is enhanced.

According to yet another illustrative aspect of the exemplary embodiment, the second inner pump electrode is made by applying to an electrolyte larger a paste that contains, as a principal ingredient, two kinds of Pt particles having different particle sizes and whose particle size ratio as measured by a sedimentation particle-size distribution ranges from 1.75 to 14.2, and which paste has a mixing ratio of large Pt particles to small Pt particles assuming a mass ratio of 50/50 to 10/90 (large Pt particles/small Pt particles) and sintering the paste.

The second inner pump electrode preferably contains 10 to 28 mass % of zirconia based on the total mass of the two kinds of Pt particles.

With such a configuration, zirconia that is the principal ingredient of the solid electrolyte layer simultaneously promotes an enhanced triple-layer interface ratio in the electrode and enhanced electrode adhesion.

This application is based on Japanese Patent Application Nos. 2008-124263 filed May 12, 2008 and 2009-071806 filed Mar. 24, 2009, the disclosures of which are incorporated herein by reference in their entirety.

What is claimed is:

1. A gas sensor including a gas sensor element extending in a longitudinal direction thereof, the gas sensor element comprising;
a first measurement chamber interposed between two solid electrolyte layers stacked with an interval therebetween and into which a gas to be measured is introduced from outside the sensor;
a first pumping cell having a first inner pump electrode facing the first measurement chamber and a first counterpart electrode for the first inner pump electrode, the first inner pump electrode being configured to control oxygen partial pressure in the first measurement chamber;
a second measurement chamber in mutual communication with the first measurement chamber, that is partitioned from surroundings and into which a gas to be measured having a controlled oxygen partial pressure is introduced from the first measurement chamber; and
a second pumping cell having a second inner pump electrode disposed within the second measurement chamber and a second counterpart electrode for the second inner pump electrode, the second pumping cell being configured to detect a specific gas component in the gas to be measured within the second measurement chamber,
wherein the second inner pump electrode is made of an aggregate that contains Pt as a principal ingredient consisting of a plurality of Pt particles,
in a cutting plane of the gas sensor element taken along its stacking direction, when a reflection electron image including an interface between the second inner pump electrode and a solid electrolyte layer in contact with the second inner pump electrode is observed, a surface of the Pt particle making up the outermost surface of the second inner pump electrode is defined as a surface to be measured, the maximum height and the minimum height between the surface to be measured of individual ones of the Pt particles and the interface are determined from a direct distance perpendicular to the interface, and
the relationships $T1-T2 \geqq 5$ and $T2/T1 \leqq 0.75$ are satisfied, wherein $T1(\mu m)$ is an average of the three largest values among the maximum heights arranged in a decreasing order from the largest value and $T2(\mu m)$ is an average of the three smallest values among the minimum heights arranged in an increasing order from the smallest value.

2. The gas sensor according to claim 1, wherein the second inner pump electrode (13*b*) contains 10 to 28 wt % of zirconia.

* * * * *